US012738363B2

(12) United States Patent
Katto et al.

(10) Patent No.: US 12,738,363 B2
(45) Date of Patent: Sep. 15, 2026

(54) HEART RATE INFORMATION CONCEALED VIDEO TRANSMISSION METHOD, PROGRAM, AND DEVICE

(71) Applicant: WASEDA UNIVERSITY, Tokyo (JP)

(72) Inventors: Jiro Katto, Tokyo (JP); Mayu Arai, Tokyo (JP); Kenji Kanai, Tokyo (JP); Yutaka Katsuyama, Tokyo (JP); Toshio Sato, Tokyo (JP); Takuro Sato, Tokyo (JP)

(73) Assignee: WASEDA UNIVERSITY, Tokyo (JP)

( * ) Notice: Subject to any disclaimer, the term of this patent is extended or adjusted under 35 U.S.C. 154(b) by 258 days.

(21) Appl. No.: 18/597,923

(22) Filed: Mar. 7, 2024

(65) Prior Publication Data

US 2024/0331846 A1 Oct. 3, 2024

(30) Foreign Application Priority Data

Mar. 27, 2023 (JP) ................................ 2023-049862

(51) Int. Cl.
*G16H 30/40* (2018.01)
*G06T 5/80* (2024.01)

(52) U.S. Cl.
CPC .............. *G16H 30/40* (2018.01); *G06T 5/80* (2024.01); *G06T 2207/10016* (2013.01); *G06T 2207/20076* (2013.01); *G06T 2207/30201* (2013.01)

(58) Field of Classification Search
CPC . G16H 30/40; G06T 5/80; G06T 2207/10016; G06T 2207/20076; G06T 2207/30201
See application file for complete search history.

(56) References Cited

U.S. PATENT DOCUMENTS 10,515,480 B1 * 12/2019 Hare ...................... G06V 20/64
11,170,578 B1 * 11/2021 Casaburo ............... G06T 7/277
11,457,271 B1 * 9/2022 Faulkner ............... H04N 7/152
11,488,293 B1 * 11/2022 Guo .......................... G06T 5/50
11,861,838 B1 * 1/2024 Gardella ............... G16H 50/20
(Continued)

FOREIGN PATENT DOCUMENTS

JP 2022128627 A 9/2022
JP 2022141565 A 9/2022
(Continued)

OTHER PUBLICATIONS

Boccignone et al. “An Open Framework for Remote-PPG Methods and Their Assessment,” IEEE Access, vol. 8, pp. 216103-216103, Dec. 2020 (https://github.com/phuselab/pyVHR). 23pp.
(Continued)

*Primary Examiner* — Mia M Thomas
(74) *Attorney, Agent, or Firm* — HAUPTMAN HAM, LLP

(57) ABSTRACT

A heart rate information concealed video transmission device includes a transmitter and a receiver. The transmitter compresses an input video and transmits the compressed video to a network, and the receiver decodes a received compressed stream, and attempts heart rate estimation by rPPG and generation of a biometric identifier. In order to invalidate heart rate estimation by a biological information processor, a corrected video generator outputs a corrected video in which small temporal variation of the input video is suppressed.

6 Claims, 18 Drawing Sheets

(56) References Cited

U.S. PATENT DOCUMENTS

| | | | | |
|---|---|---|---|---|
| 2012/0289850 | A1* | 11/2012 | Xu | A61B 5/015 600/529 |
| 2015/0055821 | A1* | 2/2015 | Fotland | G06V 10/255 382/103 |
| 2016/0196665 | A1* | 7/2016 | Abreu | G06T 11/00 345/427 |
| 2016/0269704 | A1* | 9/2016 | Ohta | H04N 23/61 |
| 2016/0284123 | A1* | 9/2016 | Hare | G06V 40/67 |
| 2017/0262994 | A1* | 9/2017 | Kudriashov | G06T 5/94 |
| 2020/0178809 | A1* | 6/2020 | Wang | A61B 5/0077 |
| 2022/0103823 | A1* | 3/2022 | Jiang | H04N 19/587 |
| 2022/0287650 | A1 | 9/2022 | Hsia et al. | |
| 2023/0359717 | A1 | 11/2023 | Nakazaki et al. | |
| 2023/0412919 | A1* | 12/2023 | Van Der Heide | A61B 5/0046 |
| 2024/0315573 | A1* | 9/2024 | Maman | A61B 5/7267 |
| 2024/0331089 | A1* | 10/2024 | Katto | G06T 3/4053 |
| 2024/0406334 | A1* | 12/2024 | Cao | G06T 17/00 |

FOREIGN PATENT DOCUMENTS

| | | | |
|---|---|---|---|
| JP | 2022177229 | A | 11/2022 |
| WO | 2021191659 | A1 | 9/2021 |

OTHER PUBLICATIONS

Seepers et al. “Attacks on Heartbeat-Based Security Using Remote Photoplethysmography,” IEEE Journal of Biomedical and Health Informatics, vol. 22, No. 3, pp. 714-721, May 2018. 9pp.

Wang et al. “Unlock with Your Heart: Heartbeat-based Authentication on Commercial Mobile Phones,” ACM IMWUT 2018, Sep. 2018. 22 pp.

Li et al. “Hiding Your Signals: A Security Analysis of PPG-based Biometric Authentication,” arXiv:2207.04434, Jul. 2022. 12pp.

* cited by examiner

FGI. 7

GOP UNIT
FRAME UNIT
133
GOP AVERAGING
FRAME AVERAGING
141
FRAME AVERAGING
$\mu(n)$
$I(n)$
134 FRAME AVERAGING
135 OFFSET ADJUSTMENT
$\mu_{GOP}$
142
$\mu_{GOP}-\mu(n)$
143
$I(n)-\mu(n)+\mu_{GOP}$
CORRECTED VIDEO

INPUT VIDEO
161
FACE DETECTION/ ROI PROCESSING
GOP UNIT
162
GOP AVERAGING
162 CORRECTION PROCESSING
FRAME AVERAGING
164
OFFSET ADJUSTMENT
165
166
CORRECTED VIDEO
ADDITIONAL INFORMATION
S(n)
FRAME UNIT

GOP UNIT
FRAME UNIT
173
GOP AVERAGING
175 OFFSET ADJUSTMENT
$\mu_{GOP}$
182
183
181
FRAME AVERAGING
FRAME AVERAGING
$\mu_{GOP}+S(n)$
$S(n)$
$S(n)$
$I(n)-\mu(n)+\mu_{GOP}+S(n)$
174 FRAME AVERAGING
ADDITIONAL INFORMATION
$S(n)$
$I(n)-\mu(n)+\mu_{GOP}$
RECORRECTED VIDEO

FIG. 15

| RATE (kbps) | HEART RATE ESTIMATION (RMSE) | | | | | | | |
|---|---|---|---|---|---|---|---|---|
| | ICA | PCA | GREEN | CHROM | POS | PBV | SSR | LGI |
| 100 | 15.51 | 17.88 | 31.87 | 22.59 | 36.08 | 24.62 | 19.99 | 31.83 |
| 200 | 19.65 | 11.12 | 19.17 | 26.24 | 29.28 | 25.91 | 11.74 | 26.55 |
| 600 | 25.41 | 20.85 | 7.26 | 8.92 | 12.42 | 28.23 | 6.56 | 10.56 |
| 1000 | 7.84 | 9.14 | 4.91 | 6.47 | 8.70 | 9.63 | 5.08 | 7.68 |
| 3000 | 7.98 | 19.96 | 5.01 | 5.26 | 5.56 | 9.63 | 5.33 | 5.18 |
| 5000 | 13.64 | 11.67 | 5.13 | 4.96 | 5.76 | 17.38 | 5.32 | 5.14 |
| NON-COMPRESSION | 7.59 | 22.58 | 4.96 | 5.10 | 5.65 | 25.63 | 5.34 | 5.13 |

FIG. 16

| RATE (kbps) | HEART RATE ESTIMATION (RMSE) | | | | | | | |
|---|---|---|---|---|---|---|---|---|
| | ICA | PCA | GREEN | CHROM | POS | PBV | SSR | LGI |
| 100 | 13.61 | 14.93 | 18.40 | 21.09 | 19.07 | 18.09 | 18.63 | 18.35 |
| 200 | 10.02 | 18.00 | 13.88 | 25.59 | 30.59 | 20.86 | 19.33 | 24.22 |
| 600 | 9.50 | 12.57 | 5.89 | 12.43 | 11.58 | 9.77 | 6.70 | 9.87 |
| 1000 | 7.52 | 6.60 | 6.05 | 8.35 | 5.72 | 5.86 | 5.34 | 5.04 |
| 3000 | 28.00 | 15.17 | 6.19 | 6.04 | 5.65 | 9.21 | 5.61 | 5.33 |
| 5000 | 9.18 | 6.08 | 5.08 | 5.14 | 5.40 | 5.22 | 5.29 | 5.08 |
| NON-COMPRESSION | 7.59 | 22.58 | 4.96 | 5.10 | 5.65 | 25.63 | 5.34 | 5.13 |

FIG. 17

| VIDEO | SESSION | HEART RATE ESTIMATION ERROR (RMSE) | | | | | | | |
|---|---|---|---|---|---|---|---|---|---|
| | | ICA | PCA | GREEN | CHROM | POS | PBV | SSR | LGI |
| ORIGINAL VIDEO | resting | 5.73 | 6.48 | 40.45 | 20.10 | 4.72 | 33.06 | 4.58 | 4.49 |
| | rotation | 14.50 | 14.95 | 32.53 | 17.51 | 15.07 | 31.71 | 16.01 | 16.98 |
| | gym | 51.34 | 46.39 | 59.70 | 54.49 | 30.44 | 51.57 | 31.22 | 50.78 |
| | talk | 20.66 | 26.72 | 36.31 | 21.61 | 40.24 | 36.00 | 37.99 | 31.09 |
| CORRECTED VIDEO | resting | 57.28 | 50.31 | 44.24 | 46.96 | 52.04 | 53.11 | 51.22 | 45.57 |
| | rotation | 32.17 | 41.54 | 57.02 | 52.03 | 45.04 | 63.76 | 55.07 | 44.39 |
| | gym | 54.89 | 54.02 | 54.29 | 57.53 | 57.40 | 59.94 | 55.52 | 58.79 |
| | talk | 39.89 | 41.56 | 45.02 | 44.96 | 48.51 | 46.81 | — | 46.91 |

FIG. 18

| VIDEO | SESSION | HEART RATE ESTIMATION ERROR (RMSE) | | | | | | | |
|---|---|---|---|---|---|---|---|---|---|
| | | ICA | PCA | GREEN | CHROM | POS | PBV | SSR | LGI |
| ORIGINAL VIDEO | resting | 3.64 | 3.94 | 3.42 | 3.32 | 3.80 | 15.73 | 3.50 | 3.36 |
| | rotation | 16.49 | 20.30 | 14.87 | 14.63 | 8.17 | 18.64 | 26.37 | 13.61 |
| | gym | 11.18 | 13.42 | 38.26 | 14.90 | 7.50 | 19.73 | 57.63 | 8.94 |
| | talk | 28.71 | 25.28 | 31.49 | 28.11 | 41.96 | 31.19 | 29.04 | 29.29 |
| CORRECTED VIDEO | resting | 29.54 | 28.36 | 65.68 | 56.55 | 36.61 | 61.60 | 38.33 | 31.03 |
| | rotation | 39.23 | 33.20 | 65.47 | 46.52 | 35.94 | 28.00 | 52.72 | 31.09 |
| | gym | 39.23 | 33.20 | 55.66 | 54.46 | 52.49 | 56.71 | 57.71 | 54.78 |
| | talk | 27.39 | 26.44 | 31.35 | 35.61 | 35.39 | 35.36 | — | 34.59 |

HEART RATE INFORMATION CONCEALED VIDEO TRANSMISSION METHOD, PROGRAM, AND DEVICE

RELATED APPLICATIONS

The present application claims the benefit of priority from the prior Japanese patent application 2023-049862 filed on Mar. 27, 2023. The entire contents of the above-captioned applications are incorporated herein by reference.

BACKGROUND OF THE INVENTION

1. Technical Field

Aspects of embodiments of the present invention relates to a heart rate information concealed video transmission method, program, and device. One aspect of embodiments particularly relates to a method and a device in which a transmission side generates and transmits a corrected video in which small fluctuation of a pixel mean value of a face region in a video signal is reduced in order to make it difficult for a reception side to estimate heart rate information of an individual in a system that transmits a video to a remote place. Another aspect of embodiments relates to a method and a device in which a transmission side generates the above corrected video and then adds additional information, and a reception side computes a pixel mean value of a face region in a video signal and then extracts the additional information added on the transmission side.

2. Description of the Related Art

In recent years, a technology called remote photoplethysmography (rPPG) for estimating a heart rate of an individual from a video signal has attracted attention. This is a non-contact technology that mainly uses an RGB camera to detect a subtle color change of a human skin surface due to a pulse, is more convenient than contact PPG that requires a dedicated measurement device, and has recently achieved estimation accuracy close to the contact PPG because of the evolution of algorithms.

In addition, Python tool for virtual heart rate (pyVHR) is an open source framework that provides rPPG-based heart rate estimation (e.g., G. Boccignone, D. Conte, V. Cuculo, A. D'Amelio, G. Grossi, and R. Lanzarotti: "An Open Framework for Remote-PPG Methods and Their Assessment," IEEE Access, Vol. 8, pp. 216103-216103, December 2020 (https://github.com/phuselab/pyVHR).). The pyVHR is a Python-based platform, and open-source-implements a plurality of rPPG methods. FIG. 1 illustrates a basic processing flow of the pyVHR. Here, an upper path is rPPG processing on a video signal, and a lower path is a path for computing a heart rate as a true value from an electrocardiogram (ECG) and a blood volume pulse (BVP) separately measured.

In FIG. 1, the rPPG performs the following process.

(1) Face detection: Cut out a face region from an input video frame using various face detection algorithms.

(2) Region of interest (ROI) processing: Further cut out a region (ROI) that contributes to heart rate estimation from the face region.

(3) RGB computation: Compute a mean value (or median value) of the ROI.

(4) Preprocessing: Perform preprocessing as necessary.

(5) rPPG: Perform various rPPG methods.

(6) Blood volume pulse estimation: Output a heart rate estimation result by using a Fourier transform method.

(7) Beats per minute (BPM) comparison: Perform comparison with a true heart rate value, and record an error or a correlation coefficient.

As a specific rPPG method, the pyVHR is provided with the following plurality of methods. At present, there is no method that is the most suitable at all times, and the tendency varies depending on an input video.

(1) Independent component analysis (ICA): Signal decomposition by independent component analysis (2) Principal component analysis (PCA): Signal decomposition by principal component analysis (3) GREEN: Green channel output (4) CHROM: Chrominance signal output (5) Plane orthogonal to skin (POS): Chrominance signal output similar to CHROM (6) Pulse blood volume (PBV): Signal decomposition based on pulse blood volume vector (7) Spatial subspace rotation (SSR): Signal decomposition based on eigenvalue decomposition (8) Local group invariance (LGI): Signal decomposition similar to SSR In addition to the heart rate estimation, biometric authentication using an interpulse interval (IPI) of consecutive heart rate has been proposed (e.g., R. M. Seepers, W. Wang, G. de Haan, I. Souedis, and C. Strydis: "Attacks on Heartbeat-Based Security Using Remote Photoplethysmography," IEEE Journal of Biomedical and Health Informatics, Vol. 22, No. 3, pp. 714-721, May. 2018.). The IPI is a time-varying variable including a certain degree of randomness, and it is known that an identifier unique to an individual and time can be derived from the IPI. This is assumed to be caused by a balance action between the sympathetic nervous system and the parasympathetic nervous system. FIG. 2 illustrates an example of a method for generating a biometric identifier by the IPI.

In FIG. 2, a sensing device measures a biological signal such as an electrocardiogram, detects a heart rate, and computes an IPI. The IPI uses 8-bit fixed-point representation. By excluding high-order bits from the identifier because of case of prediction, and similarly excluding the least significant bit from the identifier because of being susceptible to noise, a time-series vector by intermediate bits is generated. Gray coding is applied to the intermediate bit string to generate a final biometric identifier. Since this identifier is not always the same, identifiers sufficiently similar after a plurality of times of measurement are authenticated as biometric authentication. The proposal to use a heart rate for biometric authentication is also made for a contact device, for example, in L. Wang, K. Huang, K. Sun, W. Wang, C. Tian, L. Xie, and Q. Gu: "Unlock with Your Heart: Heartbeat-based Authentication on Commercial Mobile Phones," ACM IMWUT 2018 September 2018.

On the other hand, while executing rPPG remotely via a network improves convenience, an attacker can remotely acquire, from a video signal, a biometric identifier sufficiently similar to an identifier acquired by a trusted contact device. Such attacks can be made against any video communication and can pose a serious threat to biometric authentication systems using rPPG.

To address this problem, for example, L. Li, C. Chen, L. Pan, Y. Tai, J. Zhang, and Y. Xiang: "Hiding Your Signals: A Security Analysis of PPG-based Biometric Authentication," arXiv: 2207.04434, July 2022. proposes a defense method for biometric authentication using rPPG. FIG. 3 illustrates a configuration thereof. In FIG. 3, face detection and ROI processing similar to those in FIG. 1 are performed to generate a template on which a weight that temporally varies with a sine wave (different from a heart rate) is superimposed (injection template). At this time, template edges are blurred so as not to be unnaturally perceptible, and the templates are superimposed (fuzzy templates). A final corrected video is output (inject original video). Furthermore, a comparison experiment using a real video is performed by applying rPPG to a video on which correction processing is performed in comparison with a case where rPPG is applied to a video on which no correction processing is performed, whereby the accuracy of biometric authentication is successfully lowered.

However, in this method, unnatural distortion may be generated in the corrected video depending on the templates to be superimposed. In addition, a change in a time direction increases. This is expected to lead to a risk that the effect of video compression is reduced.

SUMMARY OF THE INVENTION

JP 2022-128627 A proposes a biometric authentication system using biological information including a heart rate, but does not mention anything about rPPG and a biometric authentication defense method.

JP 2022-177229 A proposes a learning method of a biometric authentication system and also refers to rPPG, but does not specifically propose anything using rPPG.

JP 2022-141565 A proposes a health monitoring system utilizing rPPG via a network, but does not propose any specific security measure.

G. Boccignone, D. Conte, V. Cuculo, A. D'Amelio, G. Grossi, and R. Lanzarotti: "An Open Framework for Remote-PPG Methods and Their Assessment," IEEE Access, Vol. 8, pp. 216103-216103, December 2020 (https://github.com/phuselab/pyVHR). described above provides a Python open source framework that performs rPPG processing on a real video, but does not mention any security measure.

R. M. Seepers, W. Wang, G. de Haan, I. Souedis, and C. Strydis: "Attacks on Heartbeat-Based Security Using Remote Photoplethysmography," IEEE Journal of Biomedical and Health Informatics, Vol. 22, No. 3, pp. 714-721, May. 2018. described above proposes biometric authentication application of rPPG and mentions that heart rate estimation close to contact PPG is possible, but proposes no specific defense method as rPPG.

L. Wang, K. Huang, K. Sun, W. Wang, C. Tian, L. Xie, and Q. Gu: "Unlock with Your Heart: Heartbeat-based Authentication on Commercial Mobile Phones," ACM IMWUT 2018 September 2018. described above proposes biometric authentication application of contact PPG, but does not mention anything about rPPG.

L. Li, C. Chen, L. Pan, Y. Tai, J. Zhang, and Y. Xiang: "Hiding Your Signals: A Security Analysis of PPG-based Biometric Authentication," arXiv: 2207.04434, July 2022. described above proposes a defense method for biometric authentication using rPPG via a network, but there is a concern about a risk that a compression rate of video compression decreases because an image is distorted according to the templates to be superimposed, or a correlation in a time direction decreases due to template superimposition.

Therefore, an object of the embodiments is to provide a heart rate information concealed video transmission method, program, and device that make it difficult for a reception side to estimate heart rate information of an individual in a system that transmits a video to a remote place.

In order to achieve the above object, an aspect of the embodiments provides the following heart rate information concealed video transmission method, program, and device.

Aspects of a first embodiment include a heart rate information concealed video transmission method including, in a system including a transmitter and a receiver and configured to transmit a video in which a person is photographed: in the transmitter, a step of generating a corrected video in which small fluctuation of a pixel mean value of a face region of the person in a video signal is reduced; and a step of transmitting the corrected video.

Aspects of a second embodiment include the he heart rate information concealed video transmission method according to the first embodiment, wherein the step of generating a corrected video includes: a step of obtaining a pixel mean value of the face region of a group of a plurality of video frames and a pixel mean value of the face region of each video frame of the group of the plurality of video frames; and a step of generating each corrected video frame by adding a difference between the pixel mean value of the video frame group and the pixel mean value of each video frame to the corresponding video frame, and generating the corrected video from a plurality of the corrected video frames.

Aspects of a third embodiment include the heart rate information concealed video transmission method according to the second embodiment, wherein the step of generating a corrected video further includes a step of adding additional information to each of the corrected video frames, and the step of transmitting the corrected video transmits a new corrected video that is a set of frames to which the additional information is added, the heart rate information concealed video transmission method including: in the receiver, a step of receiving the new corrected video; and a step of outputting a recorrected video by obtaining a pixel mean value of the face region of a group of a plurality of video frames of the received new corrected video and a pixel mean value of the face region of each video frame, restoring the additional information based on a difference value between the mean value of the video frame group and the mean value of each video frame, and adding the difference information to the video frame.

Aspects of a fourth embodiment include a heart rate information concealed video transmission program causing a computer to function as, in a system including a transmitter and a receiver and configured to transmit a video in which a person is photographed: in the transmitter, a generating unit configured to generate a corrected video in which small fluctuation of a pixel mean value of a face region of the person in a video signal is reduced; and a transmitting unit configured to transmit the corrected video.

Aspects of a fifth embodiment include the heart rate information concealed video transmission program according to the fourth embodiment, wherein the generating unit includes: an averaging unit configured to obtain a pixel mean value of the face region of a group of a plurality of video frames and a pixel mean value of the face region of each video frame of the group of the plurality of video frames; and an offset adjusting unit configured to generate each corrected video frame by adding a difference between the pixel mean value of the video frame group and the pixel mean value of each video frame to the corresponding video frame, and generate the corrected video from a plurality of the corrected video frames.

Aspects of a sixth embodiment include the heart rate information concealed video transmission program according to the fifth embodiment, wherein the generating unit further includes an adding unit configured to add additional information to each of the corrected video frames, and the transmitting unit transmits a new corrected video that is a set of frames to which the additional information is added, the heart rate information concealed video transmission program causing a computer to function as: in the receiver, a receiving unit configured to receive the new corrected video; and a recorrected video generating unit configured to output a recorrected video by obtaining a pixel mean value of the face region of a group of a plurality of video frames of the received new corrected video and a pixel mean value of the face region of each video frame, restoring the additional information based on a difference value between the mean value of the video frame group and the mean value of each video frame, and adding the difference information to the video frame.

Aspects of a seventh embodiment include a heart rate information concealed video transmission device including: a generating unit configured to generate a corrected video in which small fluctuation of a pixel mean value of a face region of a person in a video signal is reduced; and a transmitting unit configured to transmit the corrected video.

Aspects of an eighth embodiment include the heart rate information concealed video transmission device according to the seventh embodiment, wherein the generating unit includes: an averaging unit configured to obtain a pixel mean value of the face region of a group of a plurality of video frames and a pixel mean value of the face region of each video frame of the group of the plurality of video frames; and an offset adjusting unit configured to generate each corrected video frame by adding a difference between the pixel mean value of the video frame group and the pixel mean value of each video frame to the corresponding video frame, and generate the corrected video from a plurality of the corrected video frames.

Aspects of a nineth embodiment include the heart rate information concealed video transmission device according to the eighth embodiment, wherein the generating unit further includes an adding unit configured to add additional information to each of the corrected video frames, and the transmitting unit transmits a new corrected video that is a set of frames to which the additional information is added, the heart rate information concealed video transmission device as a receiver including: a receiving unit configured to receive the new corrected video; and a recorrected video generating unit configured to output a recorrected video by obtaining a pixel mean value of the face region of a group of a plurality of video frames of the received new corrected video and a pixel mean value of the face region of each video frame, restoring the additional information based on a difference value between the mean value of the video frame group and the mean value of each video frame, and adding the difference information to the video frame.

According to the embodiments, it is possible to make it difficult for a reception side to estimate heart rate information of an individual in a system that transmits a video to a remote place.

BRIEF DESCRIPTION OF THE DRAWINGS

FIG. 15 is a table illustrating comparison of heart rate estimation results by pyVHR in a case where a face video independently photographed by a web camera is compressed at different compression rates;

FIG. 16 is a table illustrating comparison of heart rate estimation results by pyVHR in a case where a face video independently photographed by a web camera is compressed at different compression rates;

FIG. 17 is a table illustrating a result of performing heart rate estimation by pyVHR using a face video dataset posted on the Internet; and FIG. 18 is a table illustrating a result of performing heart rate estimation by pyVHR using a face video dataset posted on the Internet.

DETAILED DESCRIPTION

First Embodiment (Configuration of Heart Rate Estimation/Biometric Authentication System)

Figure 4:
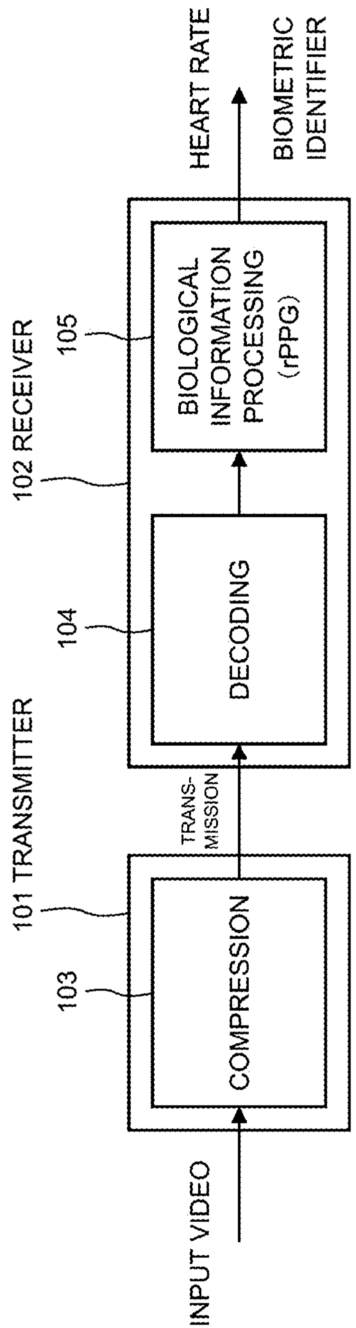
FIG. 4 illustrates a configuration example of a heart rate estimation/biometric authentication system according to a first embodiment.

FIG. 4 illustrates a configuration example of a heart rate estimation/biometric authentication system according to a first embodiment.

The heart rate estimation/biometric authentication system includes a transmitter 101 and a receiver 102. The transmitter 101 compresses an input video and transmits the compressed video to a network. The receiver 102 decodes a received compressed stream, performs heart rate estimation by rPPG, and generates a biometric identifier. A compressor 103 of the transmitter 101 performs video compression according to H.264/AVC, H.265/HEVC, or the like. A decoder 104 of the receiver 102 decodes the received compressed stream to generate a decoded video. A biological information processor 105 of the receiver 102 estimates a heart rate of a subject in the input video, and further generates the biometric identifier of the subject.

(Configuration of Biological Information Processor)

Figure 5:
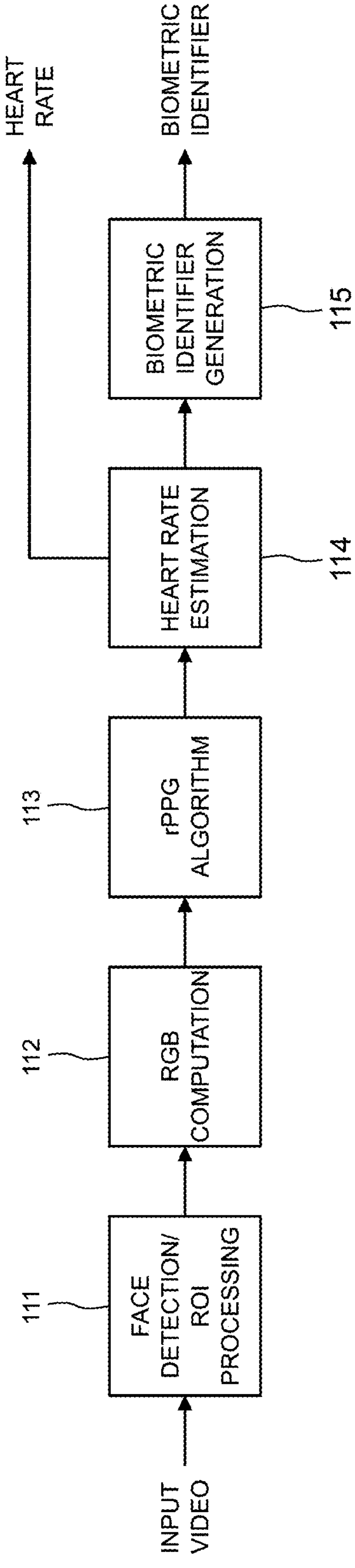
FIG. 5 illustrates a configuration example of a biological information processor.

FIG. 5 illustrates a configuration example of the biological information processor 105.

Figure 1:
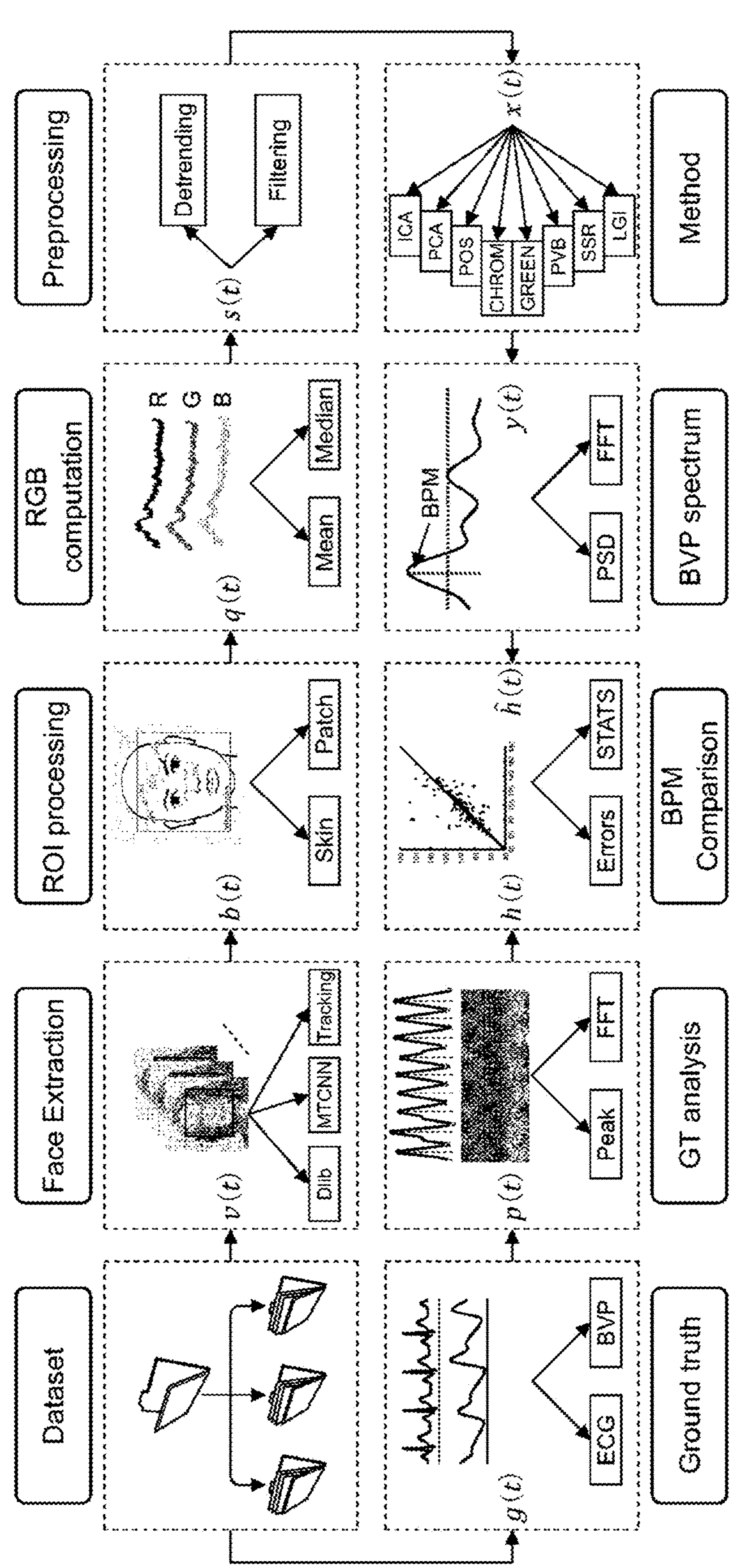
FIG. 1 is a schematic diagram for describing an example of an rPPG process.
Figure 2:
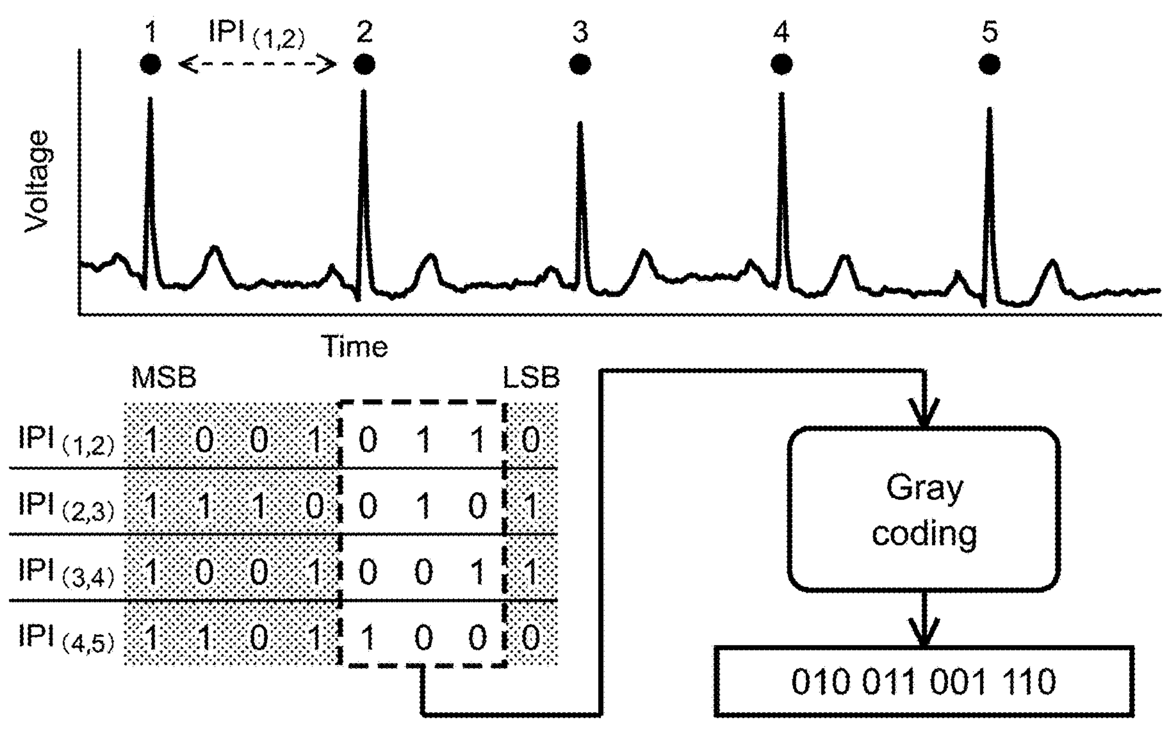
FIG. 2 is a schematic diagram illustrating an example of a method for generating a biometric identifier by IPI.

The biological information processor 105 includes a face detector/ROI processor 111, an RGB computer 112, an rPPG algorithm unit 113, a heart rate estimator 114, and a biometric identifier generator 115. Similarly to the method of FIG. 1, the face detector/ROI processor 111 detects a face region in the input video and cuts out an ROI (skin color region or patch region) necessary for heart rate estimation computation. The RGB computer 112 then computes a pixel mean value (or median value) in the ROI. The rPPG algorithm unit 113 then separates a signal corresponding to a heart rate from a temporal variation signal of the pixel mean value in the ROI. The heart rate estimator 114 then executes a Fourier transform method and outputs a heart rate estimation result. Finally, the biometric identifier generator 115 generates the biometric identifier from the time series of heart rate estimation results, similarly to the method of FIG. 2.

Figure 6:
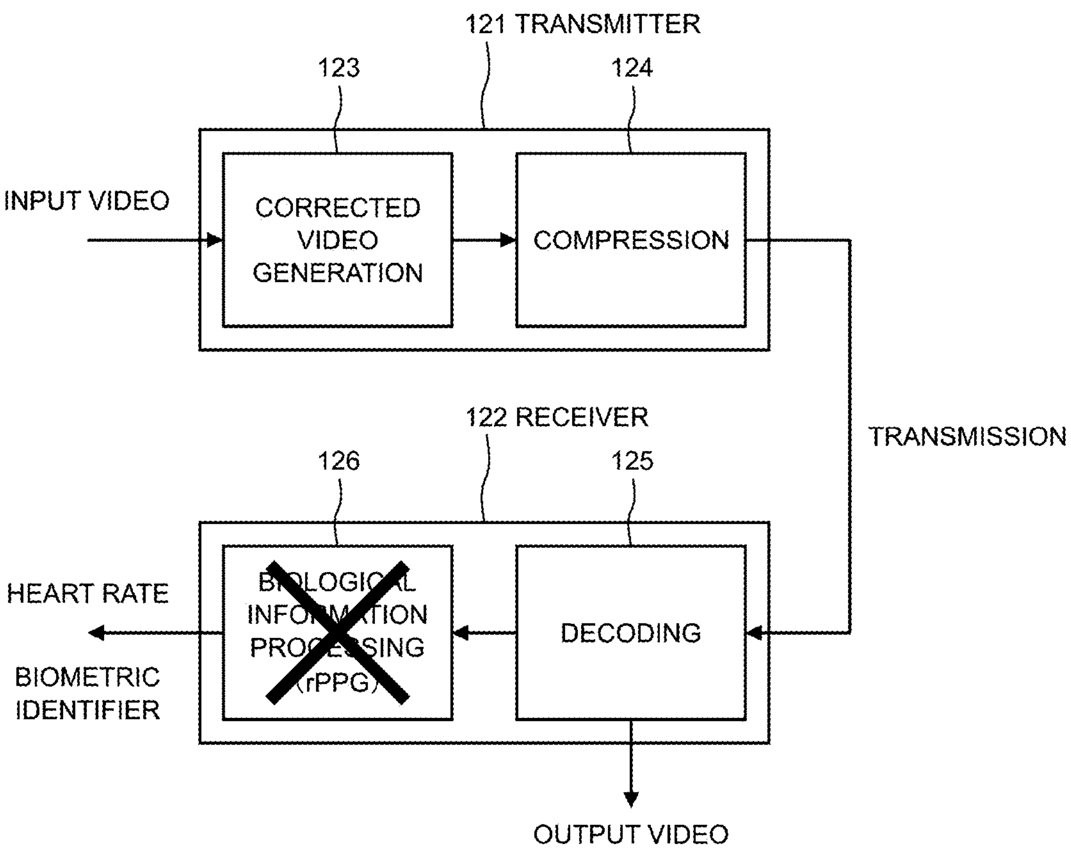
FIG. 6 illustrates a configuration example of heart rate information concealment communication according to the first embodiment.

FIG. 6 illustrates a configuration example of a heart rate information concealed video transmission device that performs heart rate information concealment communication according to the first embodiment.

Figure 3:
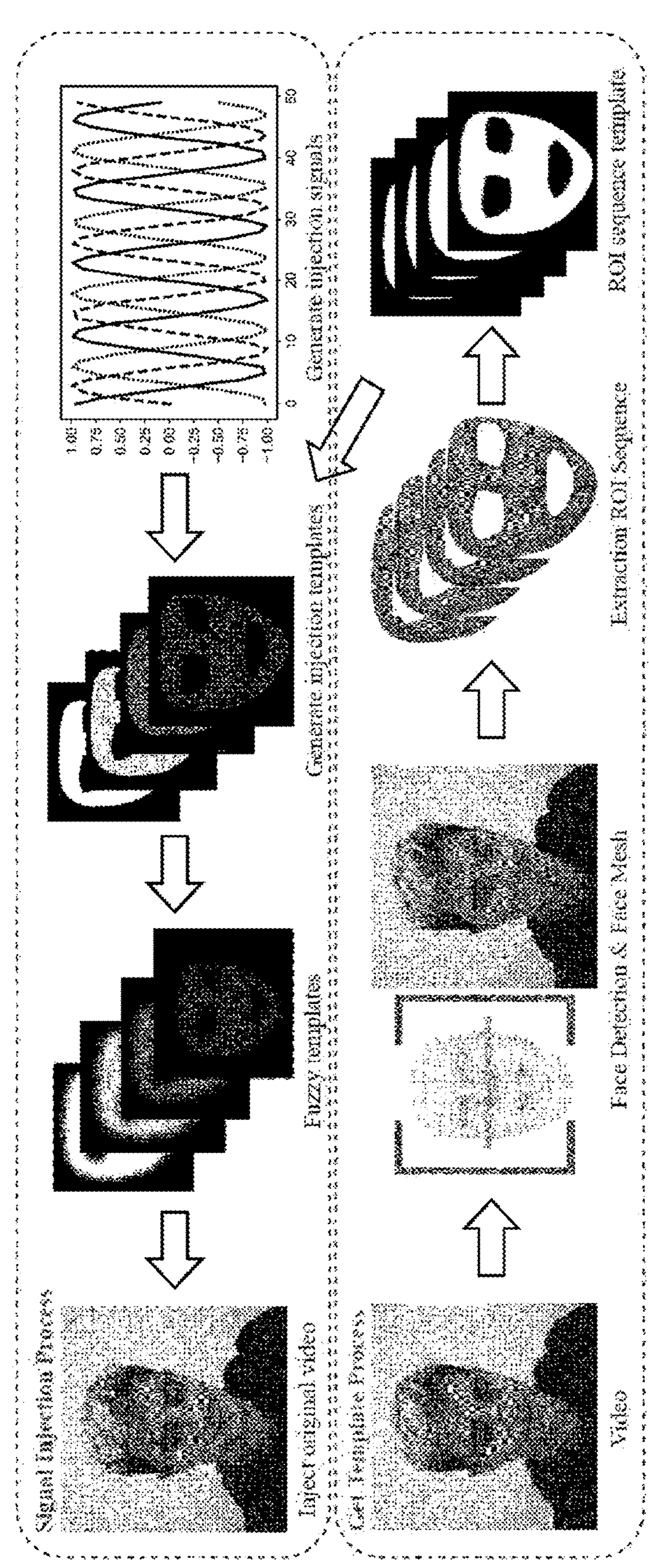
FIG. 3 is a schematic diagram illustrating an example of a defense method for biometric authentication using rPPG.

The heart rate information concealed video transmission device includes a transmitter 121 and a receiver 122. Similarly to FIG. 4, the transmitter 121 compresses an input video and transmits the compressed video to a network, and the receiver 122 decodes a received compressed stream, and attempts heart rate estimation by rPPG and generation of a biometric identifier. A compressor 124, a decoder 125, and a biological information processor 126 perform operations similar to those of the compressor 103, the decoder 104, and the biological information processor 105 in FIG. 4, respectively. In order to invalidate heart rate estimation by the biological information processor 126, a newly-added corrected video generator 123 outputs a corrected video in which small temporal variation of the input video is suppressed. Here, unlike the method of L. Li, C. Chen, L. Pan, Y. Tai, J. Zhang, and Y. Xiang: "Hiding Your Signals: A Security Analysis of PPG-based Biometric Authentication," arXiv: 2207.04434, July 2022. illustrated in FIG. 3, the pixel value of the ROI is slightly shifted instead of performing template superimposition that can be a distortion factor. This achieves a great advantage that the subjective impressions of the input video and the corrected video are equivalent and no distortion occurs.

Figure 7:
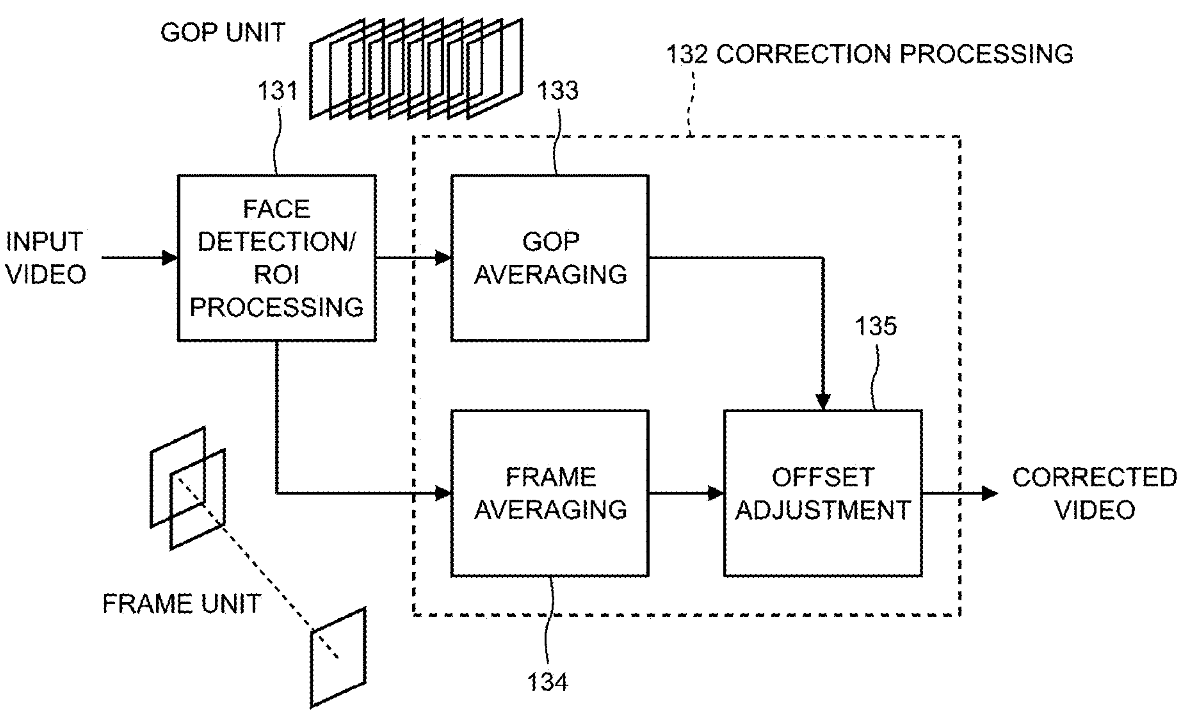
FIG. 7 illustrates a configuration example of a corrected video generator.

FIG. 7 illustrates a configuration example of the corrected video generator 123.

The corrected video generator 123 includes a face detector/ROI processor 131 and a correction processor 132. Similarly to the face detector/ROI processor 111 in FIG. 5, the face detector/ROI processor 131 detects a face region in the input video and cuts out an ROI necessary for heart rate estimation computation. The correction processor 132 includes a GOP averaging unit 133, a frame averaging unit 134, and an offset adjuster 135. First, the GOP averaging unit 133 computes a pixel mean value of a group of a plurality of video frames (GOP: Group of Pictures). The frame averaging unit 134 computes a pixel mean value of each video frame. The offset adjuster 135 receives, as input, each video frame output from the face detector/ROI processor 131, the GOP mean value output from the GOP averaging unit 133, and the mean value of the corresponding video frame output from the frame averaging unit 134, and outputs a corrected video obtained by performing offset adjustment (slight shifting of the pixel value) so that the pixel mean value of each video frame becomes equal to the pixel mean value of the GOP. The number of frames of the GOP can be set to any number such as 10, 30, or 60. Since the temporal variation of the pixel mean value of the ROI in the GOP is suppressed, it becomes difficult to perform heart rate estimation from the corrected video.

Figure 8:
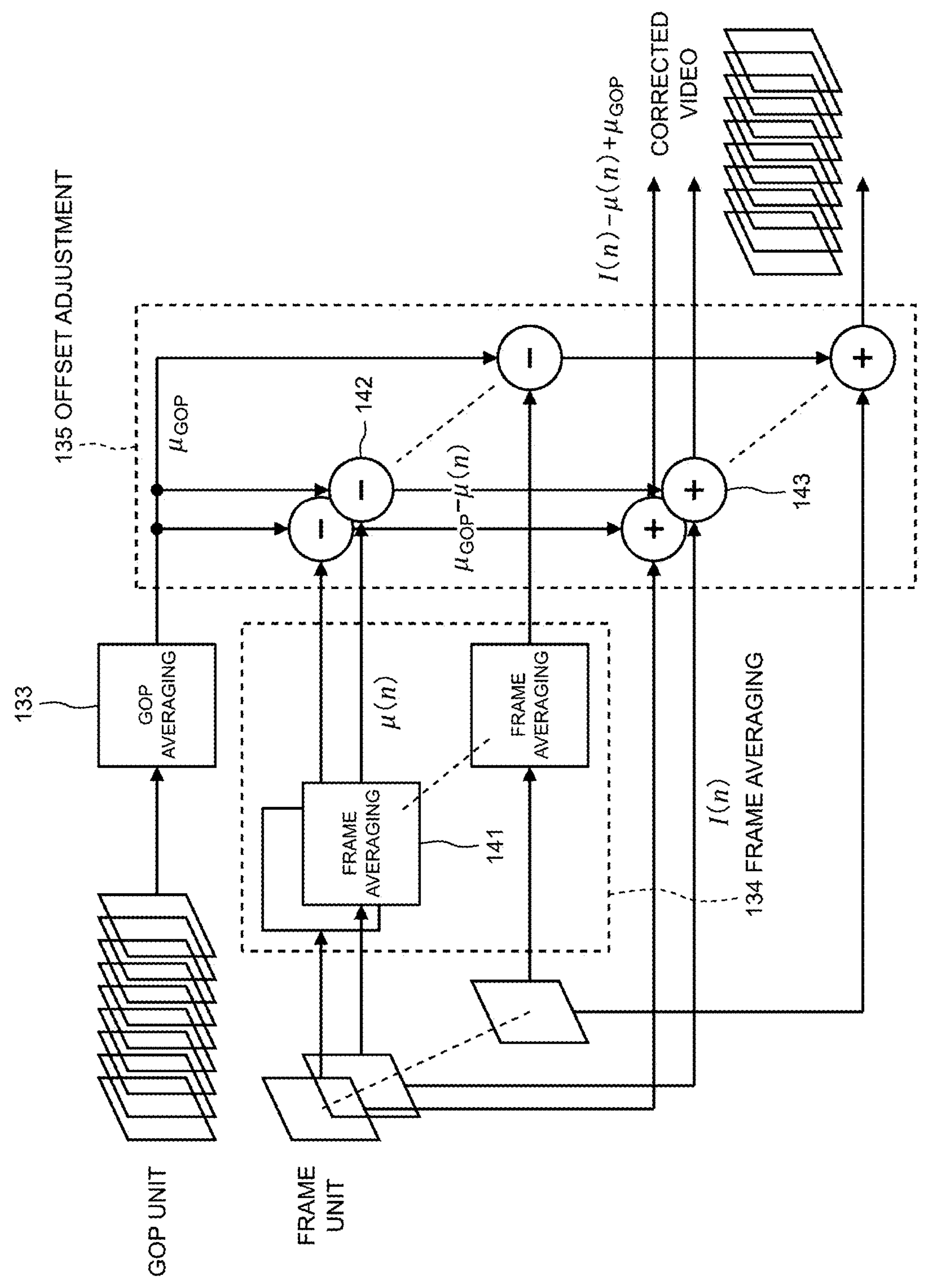
FIG. 8 illustrates a detailed configuration example of a correction processor.

FIG. 8 illustrates a detailed configuration example of the correction processor 132.

A frame averaging unit 141 of the correction processor 132 outputs the pixel mean value of the ROI of each video frame. The offset adjuster 135 of the correction processor 132 includes a subtractor 142 and an adder 143. The subtractor 142 receives the GOP mean value output from the GOP averaging unit 133, and the video frame mean value output from the frame averaging unit 141 as input, and outputs a subtraction value. The adder 143 adds the output of the subtractor 142 to the pixel value of the ROI of each video frame, and outputs the corrected video. Here, $\mu_{GOP}$, $\mu(n)$, and $I(n)$ described in FIG. 8 represent the pixel mean value of the GOP, the pixel mean value of each video frame, and the pixel value of the ROI of each frame, respectively, and n represents a frame number in the GOP (n=1, 2, . . . , N, where N is the number of video frames in the GOP). At this time, the implementation of the adder 143 can be devised in some ways. In a case where the pixel value of the corrected video is given by an integer value such as 8 bits, the simplest implementation of the adder 143 is given by the following formula.

$$I(n) = I(n) + \text{round}\,[\mu_{GOP} - \mu(n)] \quad \text{[Math. 1]}$$

Here, since $\mu_{GOP}$ and $\mu(n)$ are real values (or fixed-point representation), a rounding operation to an integer is required, and round represents the rounding operation. However, in the case of a face image with little motion, the value of $\mu_{GOP}-\mu(n)$ is very small, and in many moving images, the value becomes zero by the rounding operation. In this case, each video frame has an offset value of zero, the input video is directly output as the corrected video, and there is no concealment effect of heart rate estimation. Therefore, the following method is conceivable that avoids the above problem by converting $\mu_{GOP}-\mu(n)$ into a probability.

$$\begin{aligned} q &= \text{abs}\,(\mu_{GOP} - \mu(n)) \quad \text{[Math. 2]} \\ s &= \text{sign}\,(\mu_{GOP} - \mu(n)) \\ r &= \text{ceil}\,(q) \\ p &= q/r \\ &\text{if}\,(r \text{ and } < p) \\ I(n) &= I(n) + \text{round}\,(s * r) \\ &\text{end} \end{aligned}$$

Here, abs is an absolute value, sign is a plus/minus sign, ceil is a function for rounding to an integer, and rand is a random number from 0 to 1 generated for each pixel. In addition, in a case where $\mu_{GOP}-\mu(n)$ is referred to as offset, a variable q represents an absolute value of the offset, a variable s represents a sign of the offset, a variable r represents an integer value obtained by rounding up the offset, and a variable p represents a probability value defined by q/r. By using this method, the integer value ±r is added with the probability p, which allows for avoiding of the problem that the value becomes zero by the rounding operation, and stable suppression of the temporal variation of the pixel mean value. In addition, in a case where the variable r has a large value, thermal noise distortion may be seen in the corrected video, though this is rare in the case of a face image. A variable m satisfying p*m<1 is introduced as follows.

$$\text{if}\left(r \text{ and } < p*m\right)$$

[Math. 3]

$$I(n) = I(n) + \text{round}\left(s*r/m\right)$$

$$\text{end}$$

As a result, the addition of the variable r is the addition of r/m, and the implementation can be made subjectively imperceptible.

(Effects of First Embodiment)

According to the first embodiment described above, each video frame output from the face detector/ROI processor 131, the GOP mean value output from the GOP averaging unit 133, and the mean value of the corresponding video frame output from the frame averaging unit 134 are input, and the corrected video obtained by performing the offset adjustment (the slight shifting of the pixel value) so that the pixel mean value of each video frame becomes equal to the pixel mean value of the GOP is output. Consequently, the temporal variation of the pixel mean value of the ROI in the GOP is suppressed, and it becomes difficult to perform heart rate estimation from the corrected video, which can make it difficult for a reception side to estimate heart rate information of an individual.

In addition, unlike the method of L. Li, C. Chen, L. Pan, Y. Tai, J. Zhang, and Y. Xiang: "Hiding Your Signals: A Security Analysis of PPG-based Biometric Authentication," arXiv: 2207.04434, July 2022., the pixel value of the ROI is slightly shifted instead of performing template superimposition that can be a distortion factor. This achieves a great advantage that the subjective impressions of the input video and the corrected video are equivalent and no distortion occurs. That is, it is possible to suppress the distortion of the corrected video, and avoid a decrease in compression rate of video compression.

Second Embodiment

On the other hand, in a case where all the video frames in the GOP of the corrected video have the same mean value of pixel value of $\mu_{GOP}$ by the method or device in FIG. 6, a transmission side adds additional information to each video frame of the corrected video and transmits the information, and a reception side performs corrected video generation processing and compares the pixel mean value of the GOP and the pixel mean value of each video frame, so that the additional information can be restored. That is, the additional information can be embedded in video information and transmitted, and the additional information can be extracted on the reception side. This can be used for digital watermarking of video information, transmission of encrypted heart rate information, or the like. However, in a case where the numerical values of the information added to the respective video frames are all the same, the pixel mean value of the GOP and the pixel mean value of each video frame coincide with each other. Thus, it is necessary to take measures such as inverting the additional information of a final video frame of the GOP.

Figure 9:
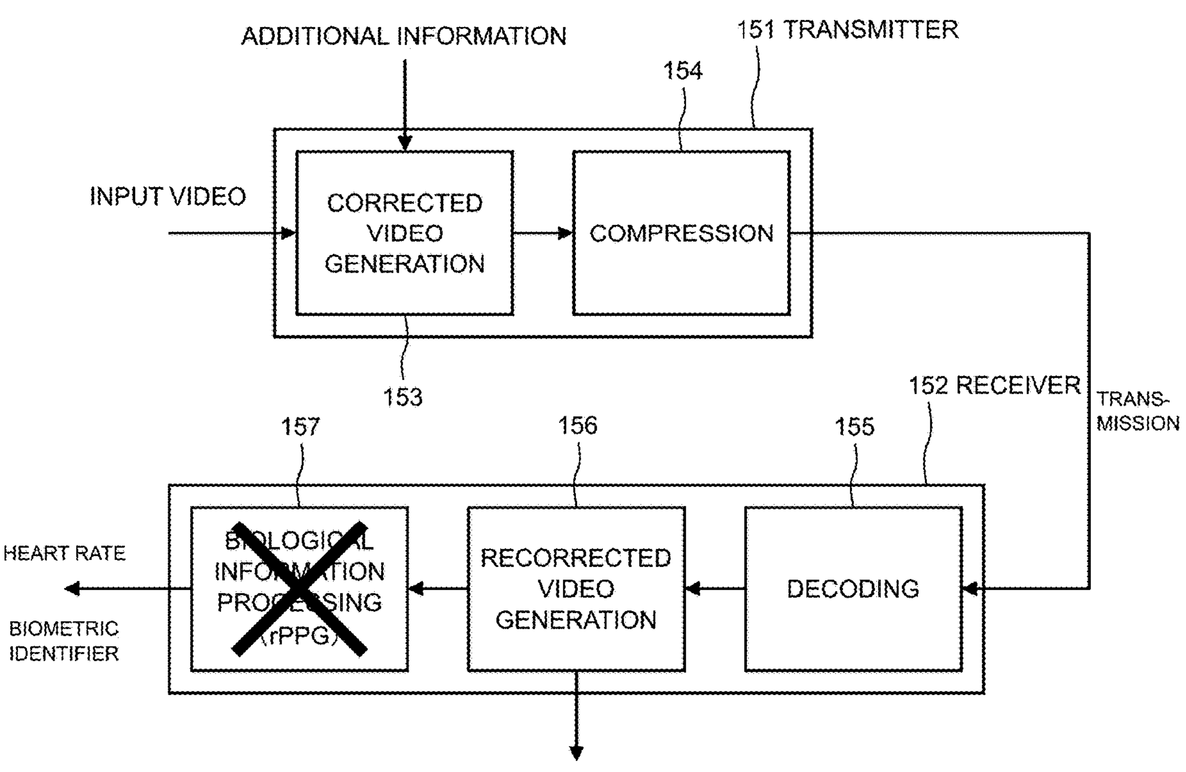
FIG. 9 illustrates a configuration example of heart rate information concealment communication according to a second embodiment.

On the basis of the above background, FIG. 9 illustrates a configuration example of a heart rate information concealed video transmission device that performs heart rate information concealment communication according to a second embodiment.

The heart rate information concealed video transmission device includes a transmitter 151 and a receiver 152. Similarly to FIG. 6, the transmitter 151 compresses an input video and transmits the compressed video to a network, and the receiver 152 decodes a received compressed stream, and attempts heart rate estimation by rPPG and generation of a biometric identifier. A compressor 154, a decoder 155, and a biological information processor 157 perform operations similar to those of the compressor 103, the decoder 104, and the biological information processor 105 in FIG. 4, respectively. In order to invalidate heart rate estimation by the biological information processor 157, a corrected video generator 153 outputs a corrected video in which small temporal variation of the input video is suppressed, and newly adds additional information to the corrected video. A recorrected video generator 156 performs an operation similar to that of the corrected video generator 153 to output a recorrected video, and also output the additional information embedded in the corrected video. Here, unlike the method of L. Li, C. Chen, L. Pan, Y. Tai, J. Zhang, and Y. Xiang: "Hiding Your Signals: A Security Analysis of PPG-based Biometric Authentication," arXiv: 2207.04434, July 2022. illustrated in FIG. 3, the pixel value of the ROI is slightly shifted instead of performing template superimposition that can be a distortion factor, similarly to the method of FIG. 6. This achieves a great advantage that the subjective impressions of the decoded video and the recorrected video are equivalent and no distortion occurs.

Figure 10:
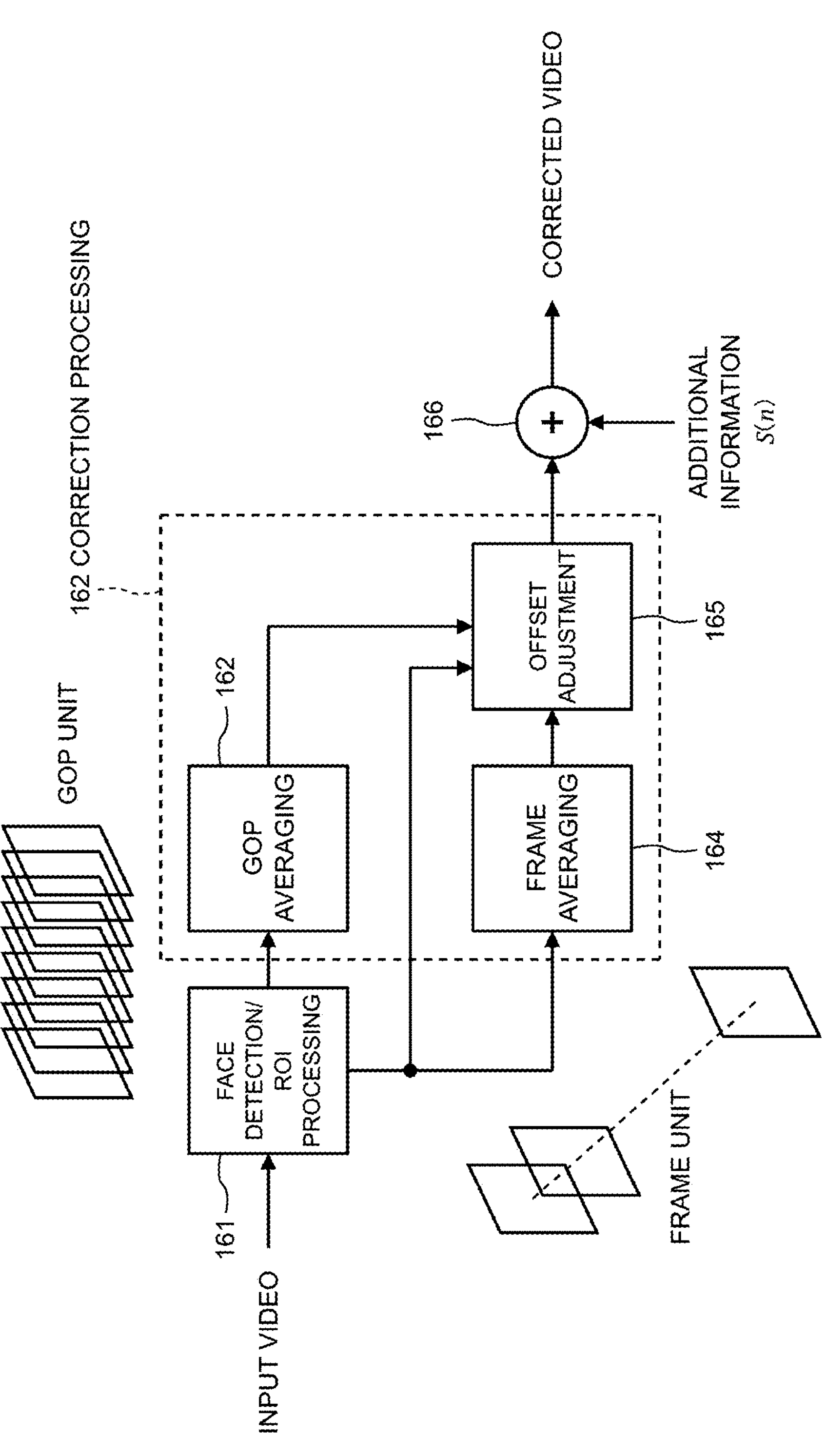
FIG. 10 illustrates a configuration example of a corrected video generator.

FIG. 10 illustrates a configuration example of the corrected video generator 153.

The corrected video generator 153 includes a face detector/ROI processor 161, a correction processor 162, and an adder 166. Similarly to the face detector/ROI processor 111 in FIG. 5, the face detector/ROI processor 161 detects a face region in the input video and cuts out an ROI necessary for heart rate estimation computation. The correction processor 162 includes a GOP averaging unit 163, a frame averaging unit 164, and an offset adjuster 165. First, the GOP averaging unit 163 computes a pixel mean value of a GOP. The frame averaging unit 164 computes a pixel mean value of each video frame. The offset adjuster 165 performs an operation similar to that of the offset adjuster 135 to receive, as input, each video frame output from the face detector/ROI processor 161, the GOP mean value output from the GOP averaging unit 163, and the mean value of the corresponding video frame output from the frame averaging unit 164, and output a corrected video obtained by performing offset adjustment (slight shifting of the pixel value) so that the pixel mean value of each video frame becomes equal to the pixel mean value of the GOP. Similarly to the first embodiment, the number of frames of the GOP can be set to any number such as 10, 30, or 60. Since the temporal variation of the pixel mean value of the ROI in the GOP is suppressed, it becomes difficult to perform heart rate estimation from the corrected video. Finally, the adder 166 adds additional information S(n) to each video frame, and generates and outputs the corrected video. Here, n represents a frame number in the GOP.

Figure 11:
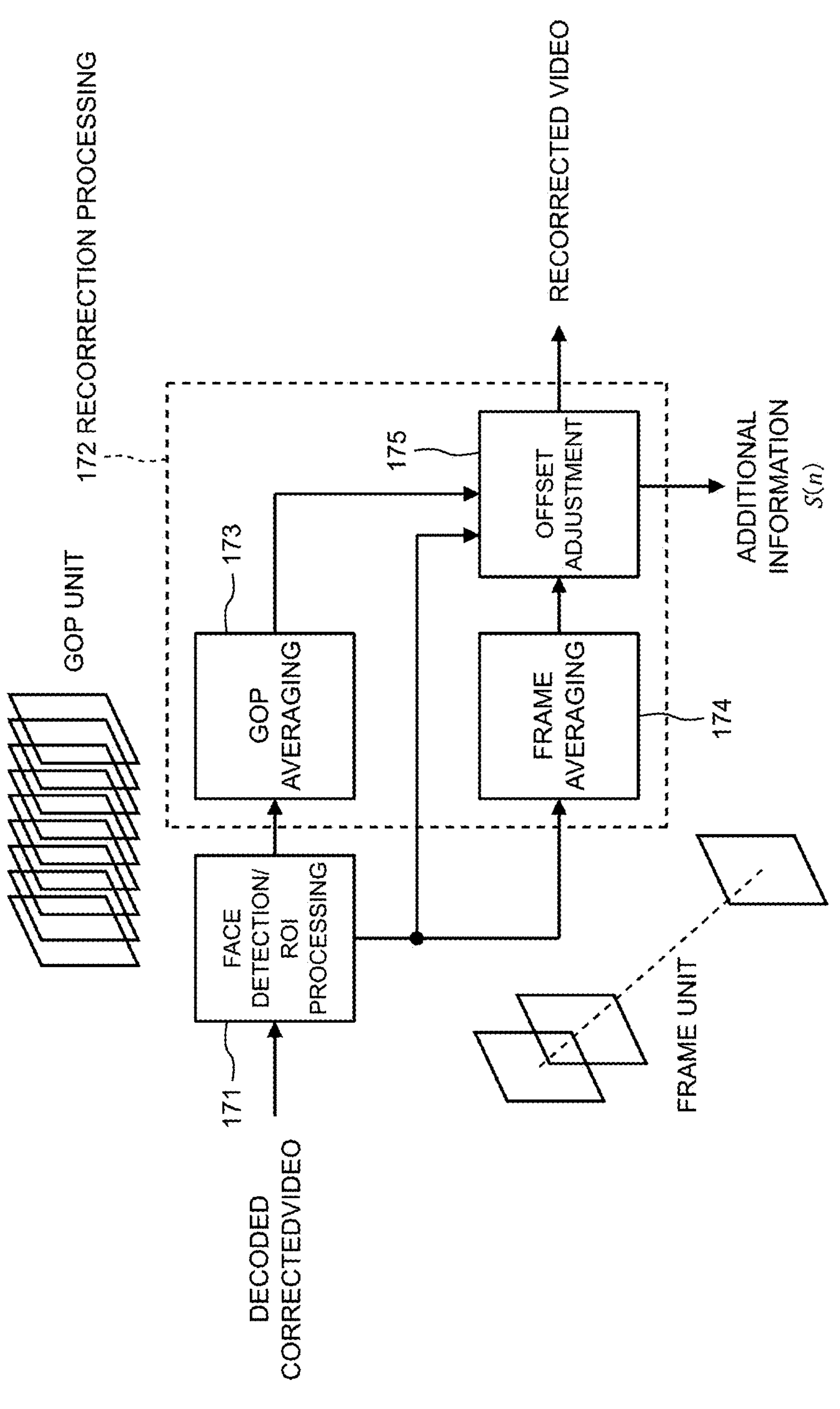
FIG. 11 illustrates a configuration example of a recorrected video generator.

FIG. 11 illustrates a configuration example of the recorrected video generator 156.

The recorrected video generator 156 includes a face detector/ROI processor 171 and a recorrection processor 172. Similarly to the face detector/ROI processor 111 in FIG. 5, the face detector/ROI processor 171 detects a face region in the input video and cuts out an ROI necessary for heart rate estimation computation. The recorrection processor 172 includes a GOP averaging unit 173, a frame averaging unit 174, and an offset adjuster 175. First, the GOP averaging unit 173 computes a pixel mean value of the GOP. The frame averaging unit 174 computes a pixel mean value of each video frame. The offset adjuster 175 receives, as input, each video frame output from the face detector/ROI processor 171, the GOP mean value output from the GOP averaging unit 173, and the mean value of the corresponding video frame output from the frame averaging unit 174, and outputs a recorrected video and extracts and outputs the additional information S(n). Here, n represents a frame number in the GOP.

Figure 12:
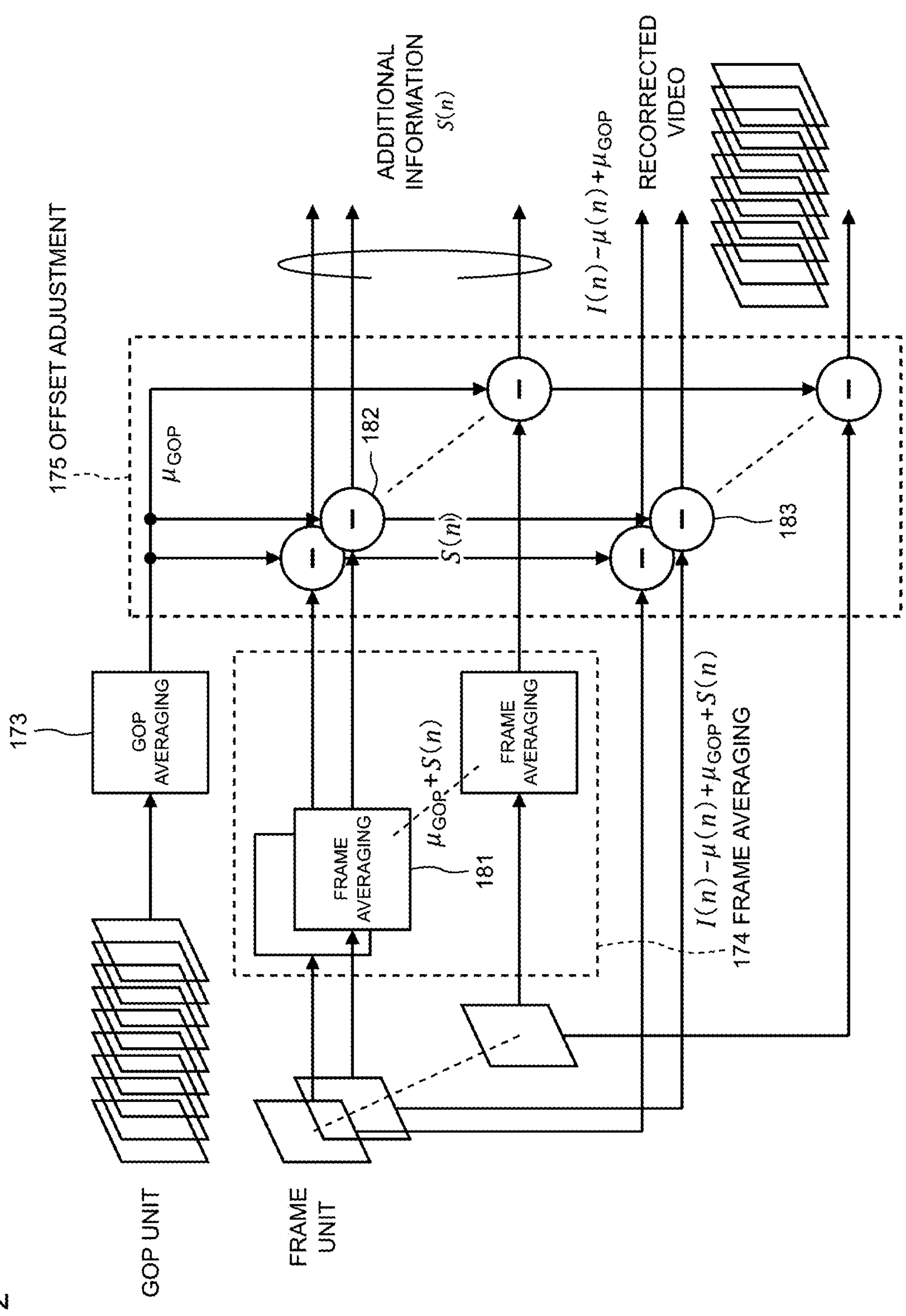
FIG. 12 illustrates a detailed configuration example of a recorrection processor.

FIG. 12 illustrates a detailed configuration example of the recorrection processor 172.

The frame averaging unit 174 of the recorrection processor 172 includes a frame averaging unit 181. The frame averaging unit 181 outputs the pixel mean value of the ROI of each video frame. The offset adjuster 175 of the recorrection processor 172 includes a subtractor 182 and a subtractor 183. The subtractor 182 receives the GOP mean value output from the GOP averaging unit 173, and the video frame mean value output from the frame averaging unit 181 as input, and outputs a subtraction value. At this time, the additional information S(n) is determined according to the sign of the subtraction value, and is output. The subtractor 183 adds the output of the subtractor 182 to the pixel value of the ROI of each video frame, and outputs the recorrected video. Here, $\mu_{GOP}$, $\mu(n)$, I(n), and S(n) described in FIG. 12 represent the pixel mean value of the GOP, the pixel mean value of each video frame, the pixel value of the ROI of each frame, and the additional information, respectively, and n represents the frame number in the GOP. The pixel mean value of each video frame is equal to $\mu_{GOP}$+S(n) by the corrected video generation on the transmission side.

Effects of Second Embodiment

According to the second embodiment described above, all the video frames in the GOP of the corrected video have the same mean value of the pixel value of $\mu_{GOP}$, the transmission side adds the additional information to each video frame of the corrected video and transmits the information, and the reception side performs the corrected video generation processing and compares the pixel mean value of the GOP and the pixel mean value of each video frame. Consequently, the additional information can be embedded in the video information and transmitted, and the additional information can be extracted on the reception side. That is, after the above corrected video generation is executed, the additional information can be added on the transmission side, and the additional information can be extracted on the reception side. This can be used for digital watermarking of video information, transmission of encrypted heart rate information, or the like.

(Example of Heart Rate Estimation/Biometric Authentication System)

FIGS. 15 and 16 are tables illustrating comparison of heart rate estimation results by pyVHR in a case where a face video independently photographed by a web camera is compressed at different compression rates.

Numerical values in the tables indicate root mean squared errors (RMSE) of heart rate estimation, and the video compression used is H.264/AVC in FIGS. 15 and H.265/HEVC in FIG. 16. The spatial resolution of the face video is 640×360. The temporal resolution is 30 fps. A true heart rate value was measured using a wearable device exclusive for heart rate measurement. As can be seen from these tables, although there is an rPPG algorithm that does not work effectively, heart rate estimation equivalent to that of a non-compressed video can be performed even in the case of a compressed video including distortion as long as the bit rate is a certain bit rate or more (600 kbps or more). It has been confirmed that similar results are obtained in the case of a 2K video (spatial resolution of 1920×1080).

Figure 13:
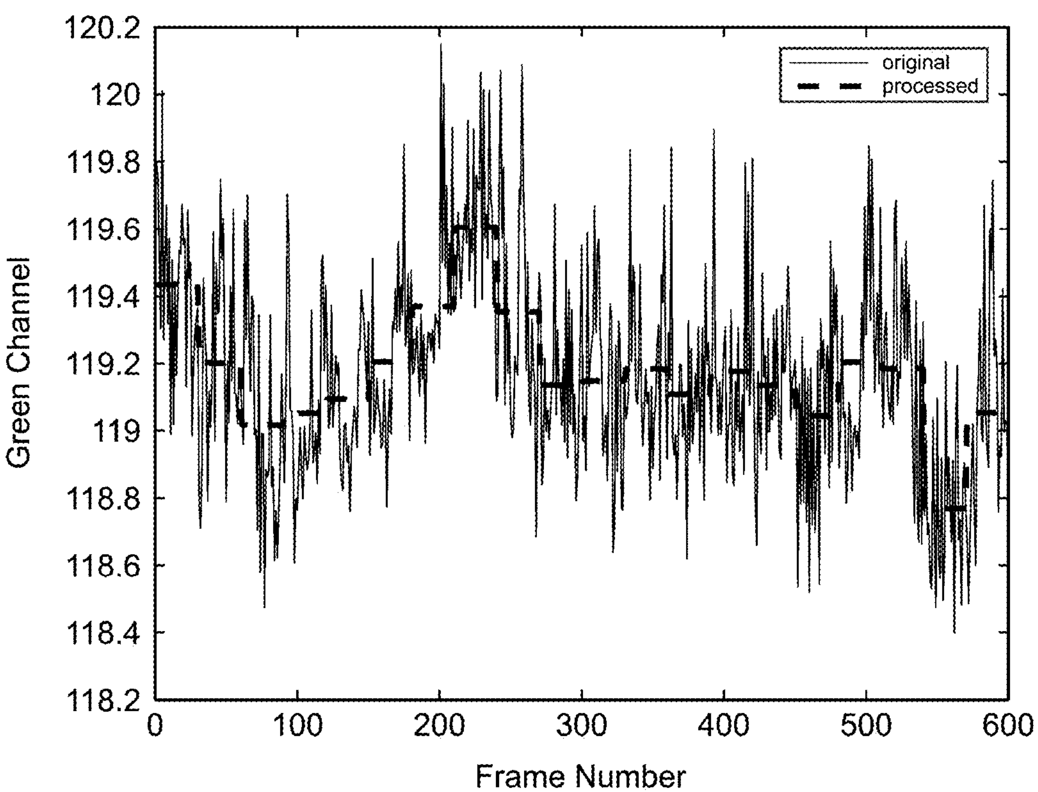
FIG. 13 is a graph illustrating comparison between a corrected video generation effect and a heart rate estimation result in the case of using a heart rate estimation method by ICA.
Figure 14:
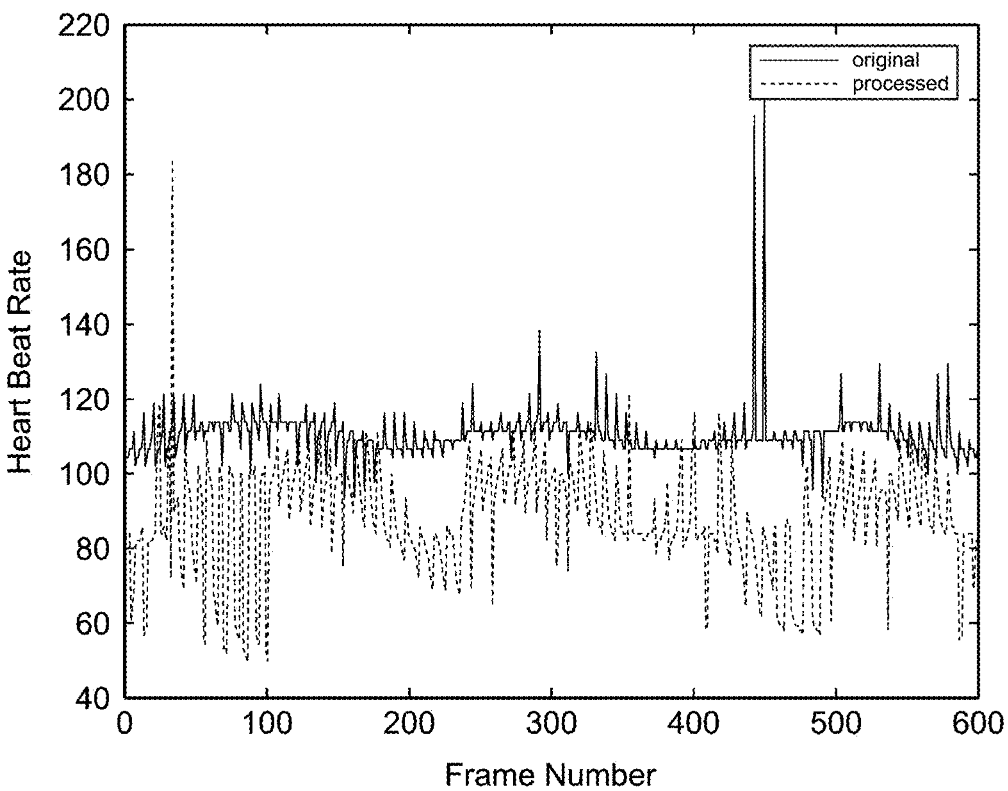
FIG. 14 is a graph illustrating comparison between a corrected video generation effect and a heart rate estimation result in the case of using a heart rate estimation method by ICA.

FIGS. 13 and 14 are graphs illustrating comparison between a corrected video generation effect and a heart rate estimation result in the case of using a heart rate estimation method by ICA.

FIG. 13 illustrates transition of the pixel mean value of a green component in the ROI of each video frame of the original face video and the pixel mean value of a green component in the ROI of each video frame of the corrected video to which the corrected video processing illustrated in FIG. 6 is applied. The number of frames of the GOP is set to 30. It can be seen that the mean value of the original video slightly varies, whereas the mean value of the corrected video has a constant value in GOP units. FIG. 14 illustrates temporal transition of results of performing heart rate estimation using the original video and the corrected video. It can be seen that the heart rate estimation result of the original video shows relatively stable numerical values, whereas the heart rate estimation result of the corrected video is not stable and has lower numerical values far from the estimation result of the original video as initially expected.

FIGS. 17 and 18 are tables illustrating a result of performing heart rate estimation by pyVHR using a face video dataset posted on the Internet.

The face video dataset posted on the Internet is LGI-PPGI-Face-Video-Database (https://github.com/partofthe-stars/LGI-PPGI-DB). The result of performing heart rate estimation by pyVHR using this dataset is shown. In this dataset, a plurality of sessions (resting, rotation, gym, talk) with different motions, places, lightings, and the like are defined, and the face videos of a plurality of subjects are recorded for each session. From this dataset, heart rate estimation experiments by pyVHR were performed using the face videos of two subjects (harun, cpi) in 4 sessions. FIG. 17 illustrates the heart rate estimation result of a subject 1, and FIG. 18 illustrates the heart rate estimation result of a subject 2. From these results, in general, a heart rate estimation error is greatly increased by the corrected video generation, and the effectiveness of the heart rate concealment purpose of the corrected video generation can be confirmed. On the other hand, depending on the session, there is a face video in which sufficient heart rate estimation cannot be performed even when the original video is used. This is a video in which the luminance of a face region photographed outdoors is dark, and is considered as a future issue of the heart rate estimation algorithms.

Other Embodiments

The present invention is not limited to the above embodiments, and various modifications can be made without departing from the gist of the present invention.

All or some of the functions of the above embodiments may be realized by a program, or may be realized by dedicated hardware for each function or hardware such as ASIC. In addition, in a case where each function is realized by a program, the program can be provided by being stored in a recording medium such as a nonvolatile memory or a CD-ROM. Replacement, deletion, addition, and the like of the above steps described in the above embodiments can be made within the scope not changing the gist of the present invention.

Moreover, each function is not necessarily realized on one device, and may be shared and realized on a plurality of devices within the scope not changing the gist of the present invention.

As described above, in a system that transmits a video to a remote place, the embodiments can achieve defense against heart rate estimation of a subject in the video and generation of a biometric identifier in the remote place without generating significant distortion in the transmitted video. Furthermore, in order to embed digital watermark or encrypted information in a video signal, the embodiments can embed additional information in the transmitted video on the transmission side and extract the embedded additional information on the reception side without generating significant distortion in the transmitted video.

What is claimed is:

1. A heart rate information concealed video transmission method comprising:

generating a corrected video based on an input video in which a person is captured, wherein small fluctuation of a pixel mean value of a face region of the person in a video signal in the input video is reduced; and transmitting the corrected video by a transmitter to a receiver in a system, wherein the method further comprising:

obtaining a pixel mean value of the face region of a group of a plurality of video frames and a pixel mean value of the face region of each video frame of the group of the plurality of video frames from the input video; and generating each corrected video frame by adding a difference between the pixel mean value of the video frame group and the pixel mean value of each video frame to the corresponding video frame, and generating the corrected video from a plurality of the corrected video frames.

2. The heart rate information concealed video transmission method according to claim 1, further comprising:

adding additional information to each of the corrected video frames;

transmitting, by the transmitter, a new corrected video that is a set of frames to which the additional information is added;

receiving the new corrected video by the receiver;

outputting a recorrected video by obtaining a pixel mean value of the face region of a group of a plurality of video frames of the received new corrected video and a pixel mean value of the face region of each video frame;

restoring the additional information based on a difference value between the mean value of the video frame group and the mean value of each video frame; and adding the difference information to the video frame.

3. A non-transitory machine readable medium containing instructions for transmitting heart rate information concealed video that, when executed, direct one or more processors to:

generate a corrected video based on an input video in which a person is captured, wherein small fluctuation of a pixel mean value of a face region of the person in a video signal in the input video is reduced; and transmit the corrected video by a transmitter to a receiver in a system, wherein the instructions further comprise, when executed, direct one or more processors to:

obtain a pixel mean value of the face region of a group of a plurality of video frames and a pixel mean value of the face region of each video frame of the group of the plurality of video frames;

generate each corrected video frame by adding a difference between the pixel mean value of the video frame group and the pixel mean value of each video frame to the corresponding video frame, and generate the corrected video from a plurality of the corrected video frames.

4. The non-transitory machine readable medium according to claim 3, the instructions further comprise, when executed, direct one or more processors to:

add additional information to each of the corrected video frames, transmit, by the transmitter, a new corrected video that is a set of frames to which the additional information is added;

receive the new corrected video by the receiver;

output a recorrected video by obtaining a pixel mean value of the face region of a group of a plurality of video frames of the received new corrected video and a pixel mean value of the face region of each video frame;

restore the additional information based on a difference value between the mean value of the video frame group and the mean value of each video frame; and add the difference information to the video frame.

5. A heart rate information concealed video transmission system comprising: at least one memory; a transmitter, a receiver, and one or more processors; and a non-transitory machine readable medium containing instructions for transmitting heart rate information concealed video that, when executed, direct the one or more processors to: generate a corrected video based on an input video in which a person is captured, wherein small fluctuation of a pixel mean value of a face region of the person in a video signal in the input video is reduced; and transmit the corrected video by the transmitter to a receiver, wherein the instructions further comprising, when executed, direct one or more processors to: obtain a pixel mean value of the face region of a group of a plurality of video frames and a pixel mean value of the face region of each video frame of the group of the plurality of video frames; generate each corrected video frame by adding a difference between the pixel mean value of the video frame group and the pixel mean value of each video frame to the corresponding video frame; and generate the corrected video from a plurality of the corrected video frames.

6. The heart rate information concealed video transmission system according to claim 5, the instructions further comprising, when executed, direct one or more processors to:

add additional information to each of the corrected video frames;

transmits, by the transmitter, a new corrected video that is a set of frames to which the additional information is added;

receive the new corrected video by the receiver;

output a recorrected video by obtaining a pixel mean value of the face region of a group of a plurality of video frames of the received new corrected video and a pixel mean value of the face region of each video frame;

restore the additional information based on a difference value between the mean value of the video frame group and the mean value of each video frame; and add the difference information to the video frame.

* * * * *